United States Patent [19]

Keller et al.

[11] Patent Number: 5,278,145
[45] Date of Patent: Jan. 11, 1994

[54] METHOD FOR PROTECTING BONE MARROW AGAINST CHEMOTHERAPEUTIC DRUGS USING TRANSFORMING GROWTH FACTOR BETA 1

[75] Inventors: Jonathan R. Keller, Frederick; Francis W. Ruscetti, Rockville; Robert Wiltrout, Frederick, all of Md.

[73] Assignee: The United States of America as represented by the Department of Health and Human Services, Washington, D.C.

[21] Appl. No.: 815,608

[22] Filed: Jan. 7, 1992

Related U.S. Application Data

[63] Continuation of Ser. No. 372,815, Jun. 29, 1989, abandoned.

[51] Int. Cl.$^5$ ............................................. A61K 37/36
[52] U.S. Cl. ..................................... 514/12; 530/399
[58] Field of Search .......................... 514/12; 530/399

[56] References Cited

PUBLICATIONS

Keller et al. "TGF—$\beta$1 Selectively Regulates Early Murine Hematopoietic Progenitors & Inhibits the Growth of IL—3 dependent Myeloid Leukemic Cell Lines," J. of Exp. Med. 168:737–750 (1988).
Sing et al. "TGF—$\beta$ Selectively Inhibits Normal & Leukemic Human Bone Marrow Cell Growth In Vitro" Blood 5:1504–1511 (1988).
Powell et al. "The Differential Inhibitary Effect of Lymphotoxin & Immune Interferon on Normal & Malignant Lymphoid Cells" Lymphokine Research 4(1) p. 13–26 (1985).
Goey, et al. The Journal of Immunology, vol. 143, Aug. 1, 1989.
Mule et al, Science 225:1487, 1984.
Lotze et al., J. Amm. Med. Assoc. 256:31117, 1986.
Moore, Immunol. Res. 8:165, 1989.
Gasparetto et al., Blood 74, 2:547, 1989.
Rosenberg et al., Scientific American, May 1990.
Neta et al., J. Immunol. 136:2483, 1986.
Castelli et al., J. Immunol. 140:3830, 1983.
Smith et al., Clinical Trials of Selected Interleukins: The Biological Response Modifiers Program Experience, First Jenner Symposium on Cytokine Interations and their control, in press, 1990.

Primary Examiner—Robert J. Hill, Jr.
Assistant Examiner—Shelly G. Cermak
Attorney, Agent, or Firm—Birch, Stewart, Kolasch & Birch

[57] ABSTRACT

The present invention relates to a method for protecting hematopoietic stem cells from the myelotoxicity of chemotherapeutic drugs or radiation therapy, which comprises, administering to a subject a therapeutically effective amount of transforming growth factor beta 1 for protecting bone marrow from the myelotoxicity of chemotherapeutic drugs or radiation therapy. The TGF$\beta$1 may be administered prior (e.g. 24 hours) to the administration of the chemotherapeutic drugs or radiation therapy. Preferably, the TGF$\beta$1 is administered to the subject in an amount of about 5 $\mu$g to 25 $\mu$g per kg body weight. The patient or subject of the present invention may be a mammal (e.g. human, domestic animal such as horse, cow, dog, cat or pig) and is preferably a human being. The mode of administration is either by interfemoral arterial, interperitoneally or subcutaneously, and preferably is by injection.

16 Claims, 3 Drawing Sheets

METHOD FOR PROTECTING BONE MARROW AGAINST CHEMOTHERAPEUTIC DRUGS USING TRANSFORMING GROWTH FACTOR BETA 1

This application is a continuation of application Ser. No. 07/372,815, filed on Jun. 29, 1989, now abandoned.

BACKGROUND OF THE INVENTION

1. Field of the Invention

The present invention relates to a method of using Transforming Growth Factor beta 1 (TGFβ1) as a chemoprotective agent for cycle active drugs such as cyclophosphimide and melphalan, and more specifically, to a method for protecting bone marrow using TGFβ1.

2. Description of Related Art

Transforming growth factor β (TGFβ1) (Roberts A. B. et al, Proc. Natl. Acad. Sci. USA, 82:119, (1985)) has been shown to both stimulate and inhibit (Sporn, M. B. et al, J. Cell Biol. 105:1039 (1987); Robey, P. G. et al, J. Cell Biol. 105:457 (1987); Centrella, M. et al, J. Biol. Chem. 262:2869 (1987); Roberts, A. B. et al, Proc. Natl. Acad. Sci. USA 82:119 (1985); Arteaga, C. L. et al, Cancer Res. 48:3898 (1988)) the proliferation of several cell types, as well as suppress a variety of cytokine-induced immunological responses (Kehrl, J. et al, J. Immunol. 137:3855 (1986); Kehrl, J. H. et al, J. Exp. Med. 163:1037 (1986); Espevik, T. et al, J. Immunol. 140:2312 (1988)). Previous studies from the laboratory of the present inventors have demonstrated that TGFβ1 selectively inhibits the proliferation and differentiation of early hematopoietic progenitor cells in vitro (Keller, J. R. et al, J. Exp. Med. 169:737 (1988); Sing, G. K. et al, Blood 72:1504 (1988)). The studies reported herein are performed to determine whether similar effects of TGFβ1 on bone marrow cells could be achieved in vivo. Since the pharmacodynamics of exogenously administered TGFβ1 have been reported to be unfavorable due to binding to serum components such as α2-macroglobulin (O'Connor, M. D. et al, J. Biol. Chem. 262:14090 (1987)) and first-pass hepatic extraction (Coffey, R. J. et al, J. Clin. Invest. 80:750 (1987)) the present inventors have developed a surgical technique to administer TGFβ1 locoregionally via injection into the femoral artery. This approach allows the determination of the in vivo effects following injection of microgram amounts of TGFβ1 on proliferation and maturation of early hematopoietic progenitor cells. The results of these studies show that relatively small amounts of TGFβ1 inhibit baseline and IL-3 (interleukin 3) driven proliferation of these progenitor cells in a time-and dose-dependent manner.

SUMMARY OF THE INVENTION

Figure 1:
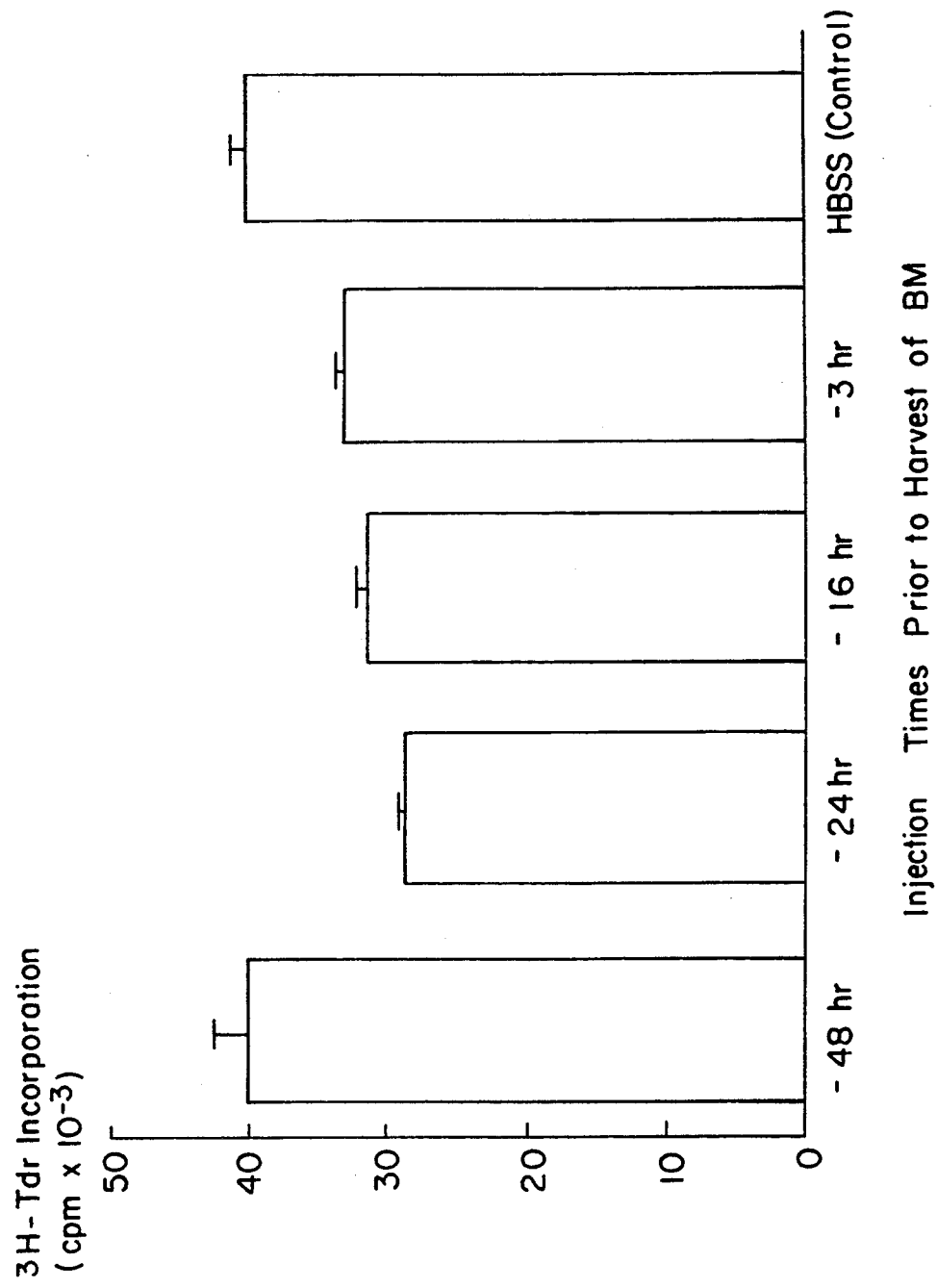
FIGS. 1 and 2 show $^3$H-Tdr incorporation as a function of injection time.

The present invention relates to a method for protecting hematopoietic stem cells from the myelotoxicity of chemotherapeutic drugs or radiation therapy, which comprises, administering to a subject a therapeutically effective amount of transforming growth factor beta 1 for protecting bone marrow from the myelotoxicity of chemotherapeutic drugs or radiation therapy. The TGFβ1 may be administered prior (e.g. 24 hours) to the administration of the chemotherapeutic drugs or radiation therapy. Preferably, the TGFβ1 is administered 3 to 72 hours prior to administration of the chemotherapeutic drug. Preferably, the TGFβ1 is administered to the subject in an amount of about 5 μg to 25 μg per kg body weight. The patient or subject of the present invention may be a mammal (e.g. human or domestic animal such as horse, cow, dog, cat or pig) and is preferably a human being. The mode of administration is interfemoral arterial, interperitoneal or subcutaneous, and preferably is by injection.

DETAILED DESCRIPTION OF THE INVENTION

Transforming growth factor-β1 (TGFβ1) has been shown in vitro to be a potent negative regulator of growth and differentiation of early hematopoietic progenitor cells, but not of more mature progenitors. However, little information is yet available regarding similar effects in vivo. The present inventors have developed an approach whereby TGFβ1 can be administered locoregionally to the bone marrow via direct injection into the femoral artery. Experiments show that intrafemoral administration of a single bolus dose of TGFβ1 potently inhibits the baseline and IL-3-driven proliferation of bone marrow cells. This inhibition is relatively selective for the earlier multipotential CFU-GEMM (e.g. granulocyte, erythroid, megakaryocyte and macrophage colony-forming units) progenitor cells since these are completely inhibited while the more differentiated CFU-C (e.g. colony-forming units assayed in culture) colonies are inhibited by about 50%. The inhibition of hematopoietic progenitor growth and differentiation is both time and dose dependent with the maximal effect on the marrow observed at 24 hours with doses $\geq 5$ μg/mouse, and the effect is reversed at later times. A practical implication of these in vivo results is the use of TGFβ1 to protect stem cells in the bone marrow from the myelotoxic effects of chemotherapeutic drugs or radiation therapy.

Myelotoxicity of bone marrow leucocyte is the major dose limiting toxicity associated chemotherapeutic drugs in cancer therapy. To maintain adequate host defense against potentially lethal infections of microorganisms, man must produce 120 million mature granulocytes every minute. Most chemotherapeutic drugs used to treat cancer destroy the body's ability to make granulocytes such that even minimally effective therapeutic doses of these drugs threaten the life of the patient. Previous attempts to alleviate this problem have centered on the use of hematopoietic growth factors ((IL-3, GM-CSF (granulocyte-macrophage colony stimulating factor) or G/CSF (granulocyte stimulating factor)) to accelerate recovery from the myelotoxicity. These agents are most effectively given after the drug and stimulate hyperactivity of the pool of stem cells left after the drug treatment. The approach of the present invention is an improvement since it is given before the drug and reduces the number of stem cells killed by the drug and reduces the amount of myelotoxicity seen. Since the number of stem cells in an individual are limited, this clinical application may produce more long-term benefits than previous therapies.

Accordingly, the present inventors have investigated whether TGFβ1 negatively regulates hematopoietic cell growth in vivo. A surgical technique has been developed to administer TGFβ1 (e.g. recombinant TGFβ1) locoregionally by injection in the femoral artery.

A summary of the surgical procedure referred to above follows. TGFβ1 is directly injected into the femoral artery thereby circumventing the first pass hepatic clearance of the TGF-β1 molecule and assuring delivery of maximal amounts of administered material to the marrow cavity. C57B1/6 mice plus or minus pre-treatment with chemotherapeutic drugs such as cyclophosphimide and melphalan are anesthetized with a 0.5 ml mixture of equal amounts of tribromyl ethyl alcohol and tertiary amyl alcohol (2.5% diluton) in PBS (e.g. phosphate buffer saline) intraperitoneally. Individual mice are placed in the supine position with the hind legs spread and fixed. After disinfection of both inguinal regions, an incision is made starting from the inner side of the thigh up to the midline of the abdomen. This procedure exposes both the femoral artery and vein in the inquinal region. A hemostat is placed onto the femoral artery, 2-3 mm caudally from the inguinal ligament and 0.02 ml of TGFβ1 +0.5% MS (e.g. mouse serum) in HBSS (e.g. Hanks' Balanced Salt Solution) is injected adjacent to the hemostat by a 1 cc syringe with a 28 G needle. Preliminary studies demonstrate that 0.02 ml per femoral artery is the maximum volume that can be injected without causing vascular damage. A Tridak Stepper is used to accurately control the volume of injection. The wound is closed with 9 mm stainless steel autoclips and the mice recover within 10 minutes.

In vivo, TGFβ1 (1-5 μg/mouse) inhibits baseline and IL-3 driven proliferation of bone marrow cells in a time and dose dependent manner. In addition, hematopoietic colony formation is assayed by CFU-GEMM, and CFU-GM formation is inhibited by TGFβ1 in vivo to the same extent as in vitro. CFU-GEMM is defined as a colony forming units that gives rise to hematopoietic colonies containing granulocytes, erythroid, monocytes and megakaryocytes; CFU-GM are cells that give rise to colonies containing granulocytes and macrophages. CFU-G are cells that give rise to colonies consisting only of granulocytes. CFU-M are cells that give rise to colonies consisting only of macrophages. Single lineage colonies, CFU-G and CFU-M, are not affected. Preliminary results suggest that a single does of TGFβ1 twenty-four hours prior to a lethal dose of cytoxan can protect the marrow from myelotoxicity and promote long-term animal survival. Thus, the selective inhibitory effect of TGFβ1 on hematopoietic cell growth is identical in vitro and in vivo, suggesting that TGFβ, and more specifically TGFβ1 is a physiological regulator of hematopoiesis may be clinically useful in protecting hematopoietic stem cells from the myelotoxicity of chemotherapeutic drugs.

The following Example is intended to illustrate the method of the claimed invention and will enable others skilled in the art to understand the invention more completely. However, the invention should not be interpreted as being limited to only this representative example.

EXAMPLE

Materials and Methods

Animals

C57B1/6 mice at 6-8 weeks of age are obtained from the animal production area of the National Cancer Institute—Frederick Cancer Research Facility (Frederick, Md.).

Growth Factors

Murine interleukin 3 (IL-3) was purified to homogeneity from WEHI-3 (a murine myelomonocyte leukemia cell line) cell supernatants using the procedures described by Ihle, J. N. et al, *J. Immunol.* 129:2431 (1982) which is herein incorporated by reference. Human recombinant erythropoietin (Epo) was purchased from Amgen Corporation, Thousand Oaks, Calif. Human recombinant TGFβ1 (rHu-TGF-β1) was a generous gift from Dr. M. Palladino, Jr., Genentech. Inc., South San Francisco, Calif. Natural TGF-β can be obtained in sufficient quantities to purify from human and porcine platelets and bovine bone (Roberts, A. B. et al, *Biochemistry*, 22:5692-5698 (1983); Cheifetz, S. et al, *Cell.* 48:409-415 (1987); Seyedin, S. M. et al, *Proc. Natl. Acad. Sci. USA.* 82:2267-2271 (1985)). Purified recombinant TGF-β can be obtained using expression vector containing the gene encoding for TGF-β stably introduced into Chinese hamster ovary cells (Gentry, L. E. et al, *Molec. Cell. Biol.*, 7:3418-3427 (1987)).

Assessment of Proliferation of Bone Marrow Cells

Bone marrow cells are aspirated from the femurs of control or TGFβ1-pretreated C57B1/6 mice with RPMI 1640 (Roswell Park Memorial Institute). The cells are then washed twice and resuspended in RPMI 1640 containing 10% fetal bovine serum (FCS) (Hyclone, Logan, Ut.) with or without IL-3 (100 U/ml) and seeded into 96-well microtiter plates (Costar, Cambridge, Mass.) at 10 cells in 100 μl of medium. Proliferation is assessed after 72 hours of incubation, unless otherwise indicated, at 37° C. in 5% $CO_2$ by an overnight pulse of 1 μCi $^3$H thymidine (Tdr) /well (6.7 Ci/mmol) (New England Nuclear, Boston, Mass.). Cell cultures are harvested on glass fiber filters using a PHD cell Harvester (Cambridge Technology, Inc., Mass.). Individual filters are placed in 2 ml Betafluor scintillation liquid (National Diagnostics, Manville, N.J.) and radioactivity is assessed by liquid scintillation counting. Counts are expressed as the mean±standard error of the mean of triplicate cultures.

Soft Agar Colony Forming Assay

The assay to measure colony formation of bone marrow cells is carried out as described by Lu, L. et al., *Blood* 61:250 (1983) which is herein incorporated by reference. Briefly, bone marrow cells from C57B1/6 mice are plated at $10^5$ cells/ml in 35 mm Lux petri dishes (Miles Laboratories, Inc., Naperville, Ill.) containing a 1 ml mixture of RPMI 1640, 20% FCS (e.g. fetal calf serum), 1% L-glutamine, $2 \times 10^{-4}$M hemin, 2 U/ml Epo, 100 U/ml IL-3, and 0.05 mg/ml gentamicin in 0.3% Seaplaque agarose (FMC Bioproducts, Rockland, Me.). Dishes are incubated at 37° C. in 5% $CO_2$ and scored for colony growth (CFU) after 7 and 14 days. Multipotential colonies containing granulocyte, erythroid, megakaryocyte and macrophage lineages are designated CFU-GEMM, while monocyte, myeloid, and myelomonocytic colonies are designated as colony forming units assayed in culture (CFU-GM).

Locoregional Administration of TGFβ1

Because several branches of the femoral artery serve as the blood supply to the femur and subsequently to the bone marrow, a surgical technique has been devised to inject TGFβ1 directly into the femoral artery thereby circumventing the first pass hepatic clearance of the molecule (Coffey, R. J. et al., *J. Clin. Invest.* 80:750 (1987)) and assuring delivery of maximal amounts of administered material to the marrow cavity. C57B1/6 mice are anesthetized with a 0.5 ml mixture of equal amounts of tribromyl ethyl alcohol and tertiary amyl alcohol (2.5% dilution) in phosphate buffer saline (PBS) intraperitoneally. Individual mice are placed in the supine position with the hind legs spread and fixed. After disinfection of both inguinal regions, an incision is made starting from the innerside of the thigh up to the midline of the abdomen. This procedure exposes both the femoral artery and vein in the inguinal region. A hemostat is placed onto the femoral artery, 2–3 mm caudally from the inguinal ligament and a 0.02 ml of TGF$\beta$1+0.5% MS in HBSS is injected adjacent to the hemostat by a 1 cc Plastipak syringe with a 28 G needle (Becton-Dickinson, Mountain View, Calif.). Preliminary studies demonstrate that 0.02 ml per femoral artery is the maximum volume that can be injected without causing vascular damage. By using a Tridak Stepper (Brookfield Center, Conn.) the volume of injection is accurately controlled. After the injection, a Q-tip (e.g. cotton swab) is used to prevent bleeding at the injection site. The wound is closed with 9 mm stainless steel autoclips and the mice recover from the procedure within 10 minutes. No procedure-related deaths result from this technique. Delivery of reagents to the bone marrow (BM) is confirmed by preliminary studies using India ink. One and 24 hours after the injection, the dye is detected in the femur and locoregionally but not systemically.

Results

Inhibition of Progenitor Cell Proliferation as a Function of Time

To determine the inhibitory effects of TGF$\beta$1 on bone marrow proliferation and differentiation in vivo. 15 $\mu$g of rhu TGF$\beta$1 is injected into the femoral arteries of normal C57B1/6 mice (7.5 $\mu$g per femoral artery), 3, 16, 24, and 48 hours prior to sacrifice of the mice. The results shown in FIG. 1 demonstrate that administration of TGF$\beta$1 24 hours prior to assay, inhibits baseline proliferation of bone marrow cells by 55% (p<0.01). The proliferative response recover by 48 hours.

Figure 2:
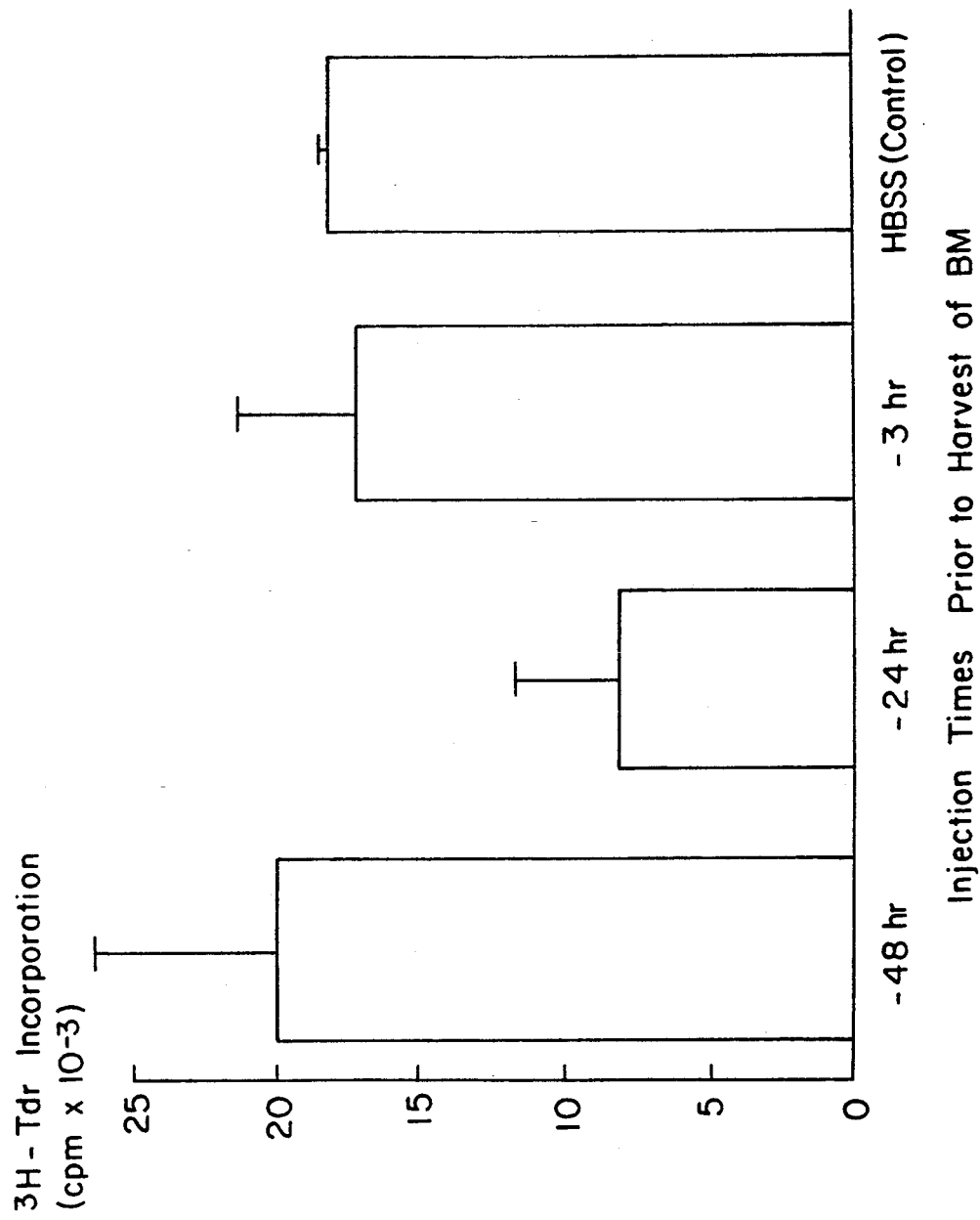

Since it has been previously shown that TGF$\beta$1 also inhibits IL-3 driven bone marrow proliferation in vitro (Keller, J. R., et al. *J. Exp. Med.* 169:737 (1988)), bone marrow cells are harvested from control and TGF$\beta$1-treated mice and then cultured in the presence of IL-3 in vitro for 72 hours (FIG. 2). The results demonstrate that the IL-3 driven proliferation of bone marrow cells is inhibited by 30% (p<0.01) compared to the control group, when TGF$\beta$1 is administered 24 hours prior to bone marrow harvest. This inhibitory effect is again lost by 48 hours after TGF$\beta$1 injection.

The quantitative difference in inhibition between the IL-3 driven and non-IL-3 driven proliferation (30% vs. 55%, respectively) might be the result of the overall stimulatory effects of IL-3 on all progenitors, including those inhibited or not inhibited by TGF$\beta$1 (Spivak, J. L. et al, *J. Clin. Invest.* 76:1613 (1985); Lord, B. I. et al, *Lymphokine Res.* 5:97 (1986)). Therefore, studies are performed in parallel to also determine the effect of in vivo administration of TGF$\beta$1 on the proliferation and differentiation of various progenitor cells by measuring the effects on formation of soft agar colonies. The results shown in Table I demonstrate the CFU-C in cultures containing IL-3 and Epo are inhibited by 76% when mice are treated 24 hrs earlier with TGF$\beta$1.

TABLE I

Effects of Locoregionally Delivered TGF$\beta$1 on Hematopoietic Colony Formation in Soft Agar as a Function of Time

| Injection times[a] prior to harvest | CFU-c[b] | CFU-GEMM[b] |
|---|---|---|
| −48 hr | 50 ± 8[d] | 2 ± 1 |
| −24 hr | 16 ± 7[c] | 0 |
| −3 hr | 46 ± 5[c] | 1 ± 1 |
| HBSS (Control) | 67 ± 5 | 5 ± 1 |

[a]There are four mice per group. Each mouse receives 15 $\mu$g of TGF$\beta$1. These data are representative of three separate experiments.
[b]CFU-c and CFU-GEMM colonies are assayed as described in the Materials and Methods, in presence of 100 U/ml IL-3 and 2 U/ml Epo, and scored after 7 and 14 days.
[c]Significantly less than HBSS(control), p ≤ 0.01
[d]Significantly less than HBSS(control), p ≤ 0.05.

Formation of granulocyte, erythroid, megakaryocyte and macrophage colony-forming units (CFU-GEMM) colonies, which represent one of the earliest progenitor cells detectable in vitro, is inhibited completely. The sixteen colonies that are formed from bone marrow cultured 24 hrs after TGF$\beta$1 administration are all of a single myeloid lineage. These results are similar to those previously reported following in vitro treatment of bone marrow cells with TGF$\beta$1 (Keller, J. R. et al., *J. Exp. Med.* 169:737 (1988)). In contrast to the effects of TGF$\beta$1 on overall proliferation of bone marrow cells, the inhibition of progenitor cell growth is not only evident at 24 hrs, but is also demonstrable by 3 hrs post treatment, and some inhibition of growth remains at 48 hrs post treatment. These results suggest that the progenitor cells are more sensitive to the effects of TGF$\beta$1 than are more mature cells.

Figure 3:
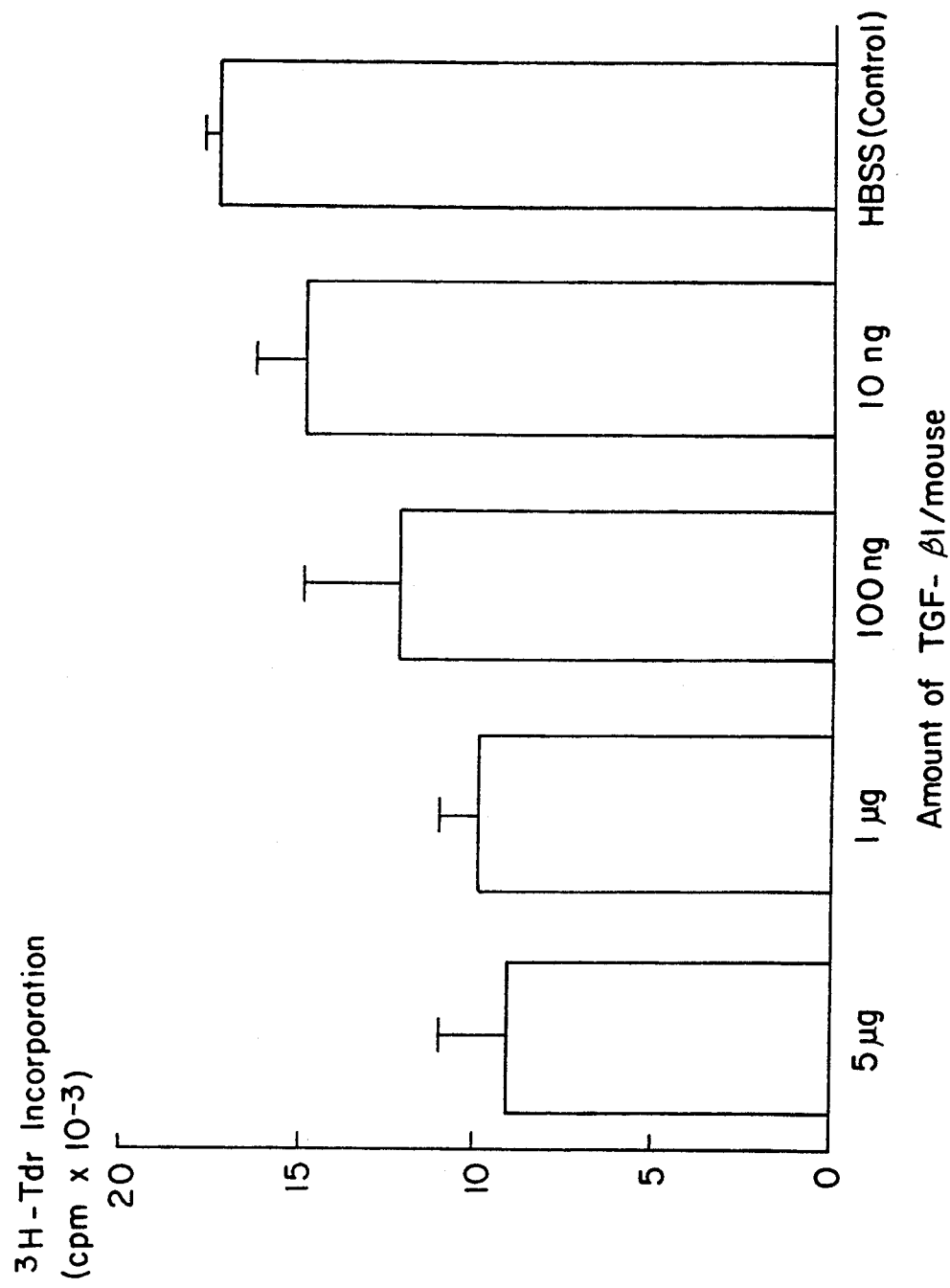
FIG. 3 shows $^3$H-Tdr incorporation as a function of the amount of TGF-β1/mouse.

Dose Dependency of Locoregionally Administered TGF$\beta$1 on Proliferation and Colony Forming Ability of Hematopoietic Progenitor Cells The time course studies performed in FIGS. 1, 2 and Table I use the maximal amount of TGF$\beta$1 (15 $\mu$g) that can be administered in 0.04 ml (7.5 $\mu$g in 0.02 ml per femoral artery). Therefore, subsequent studies are designed to determine whether lower doses of TGF$\beta$1 could have similar inhibitory effects on bone marrow stem cells when they are pretreated in vivo for 24 hours. In the experiment shown in FIG. 3, mice are injected with decreasing amounts of TGF$\beta$1 intra-arterially. The baseline proliferation of bone marrow cells is significantly inhibited by 43% at 1 $\mu$g (p<0.001) and 48% at 5 $\mu$g (p<0.001) per mouse. TGF$\beta$1 doses of 10 ng and 100 ng/mouse do not significantly inhibit bone marrow cell proliferation. The levels of inhibition observed at 1–5 $\mu$g/mouse TGF$\beta$1 are similar to those previously observed for 15 $\mu$g/mouse TGF$\beta$1 when given 24 hours prior to assay. In subsequent experiments, it is demonstrated that doses of TGF$\beta$1>5 $\mu$g/mouse do not further inhibit proliferation of bone marrow cells. Thus, within the context of the amounts of TGF$\beta$1 that could be administered, it is concluded that doses of TGF$\beta$1>5 $\mu$g/mouse induce maximal inhibition of bone marrow cell proliferation. By contrast, after in vitro exposure to TGF$\beta$1, the plateau of maximal inhibitory effects occurs at less than 1$\mu$g/ml (Keller, J. R. et al., *J. Exp. Med.* 169:737 (1988)).

Parallel studies of colony forming ability are shown in Table II below.

TABLE II

Dose Dependent Effects of Locoregionally Delivered TGFβ1 on Hematopoietic Colony Formation in Soft Agar

| TGFβ1 injected per mouse[a] | CFU-c | CFU-GEMM[b] |
|---|---|---|
| 5 μg | 44 ± 9[c] | 0 |
| 1 μg | 62 ± 3[c] | 2 ± 0 |
| 0.1 μg | 64 ± 8[d] | 3 ± 0 |
| 50 ng | 77 ± 6 | 2 ± 1 |
| 10 ng | 81 ± 8 | 5 ± 4 |
| HBSS (control) | 85 ± 9 | 5 ± 2 |

[a]There are three mice per group. These data are representative of three separate experiments.
[b]CFU-c and CFU-GEMM colonies are assayed as described in the Material and Methods, in presence of 100 U/ml IL-3 and 2 U/ml Epo, and scored on day 7 and 14, respectively.
[c]Significantly less than HBSS (control), $p \leq 0.01$.
[d]Significantly less than HBSS (control), $p \leq 0.05$.

The parallel studies of colony forming ability (Table 2) reveal that a dose of 5 μg/mouse of TGFβ1 inhibits (p<0.01) by 45% the number of CFU-C and totally inhibits the formation of CFU-GEMM. The dose of 1 μg/mouse also significantly (p<0.01) inhibits formation of CFU-C and CFU-GEMM. Doses of TGFβ1 of less than 0.1 μg/mouse do not significantly inhibit colony forming units. As in previous experiments (Table I), the colonies remaining after TGFβ1 treatment at the highest dose (5 μg/mouse) are single lineage myeloid colonies. These results demonstrate that the locoregional administration of relatively small amounts ($\geq 5 \mu g$/mouse) of TGFβ1 has profound transient effects on hematopoietic stem cells.

Discussion

TGFβ1 is a molecule with pleiotropic biological effects. It has been shown to either stimulate or inhibit cell proliferation, differentiation, or other critical cell functions in vitro (Sporn, M. B. et al, *J. Cell Biol.* 105:1039 (1987); Robey, P. G. et al, *J. Cell Biol.* 105:457 (1987); Centrella, M. et al, *J. Biol. Chem.* 262:2869 (1987); Roberts, A. B. et al, *Proc. Natl. Acad. Sci. USA* 82:119 (1985); Arteaga, C. L. et al, *Cancer Res.* 48:3898 (1988); Kehrl, J. H. et al, *J. Immunol.* 137:3855 (1986); Kehrl, J. H. et al, *J. Exp. Med.* 163:1037 (1968); Espevik, T. et al, *J. Immunol.* 140:2312 (1988)).

The demonstration by Ellingsworth, et al. (*J. Biol. Chem.* 261:12362 (1986)) that significant quantities of TGFβ1 are produced in the bone marrow and hematopoietic progenitors of the fetal liver stimulated interest in the possibility that TGFβ1 might be involved in the regulation of hematopoietic cell growth and differentiation. Subsequently, Keller, et al. (*J. Exp. Med.* 169:737 (1988)) demonstrated that TGFβ1 is indeed a potent selective negative regulator of early hematopoietic progenitor cell growth and differentiation, while exhibiting minimal effects on more mature progenitor cells. In virtually all studies to date, the inhibitory effects of TGFβ1 are reversible and cytostatic rather than cytotoxic. (Sing, G. K. et al, *Blood* 72:1504 (1988); Shipley, G. D. et al, *Cancer Res.* 46:2068 (1986)).

Most of the above effects of TGFβ1 have been studied with in vitro systems and relatively little is known about the actual effects of this molecule in vivo although Russell, et al. (*Proc. Natl. Acad. Sci. USA* 85:5126 (1988)) have shown recently that TGFβ1 can inhibit the early proliferative component of liver regeneration after partial hepatectomy when injected in vivo. These results suggest that TGFβ1 might play an important role both for the proliferative response of liver regeneration and for the subsequent restraint of liver proliferation that prevents overgrowth.

The present inventor's approach to understanding at least some of the biological effects of TGFβ1 in vivo has been to develop a model for observing the effects of optimal delivery to the bone marrow. The rationale for such an approach is that it provides favorable local biodistribution without the need to confront problems associated with systemic administration of this molecule. A lack of effect on the bone marrow following locoregional administration would suggest that systemic administration would probably to fruitless. In vivo data TGFβ1 is given locoregionally at 24 hours prior to BM-cell harvest, even relatively small amounts (1 to 5 μg/mouse) can selectively and reversibly inhibit growth and differentiation of early hematopoietic progenitor cells (see Table II). Even smaller amounts of TFGβ1 would possibly be effective if it was not for the rapid binding to α2-macroglobulin (O'Connor, M. D. et al, *J. Biol. Chem.* 262:14090 (1987)) and the fact that many cells in the blood express receptors for TGFβ (Kehrl, J. H. et al, *J. Immunol.* 137:3855 (1988); Kehrl, J. H. et al, *J. Exp. Med.* 163:1037 (1986); Espevik, T. et al, *J. Immunol.* 140:2312 (1988); Keller, J. R. et al, *J. Exp. Med.* 169:737 (1988); Sing, G. K. et al, *Blood* 72:1504 (19BB); Sporn, M. B. et al, *Nature* 332:217 (1988); Ellingsworth, L. R. et al, *Cell Immunol.* 114:41 (1988); Smeland, E. B. et al, *Exptl. Cell Res.* 171:213 (1987)). These two circumstances probably serve to rapidly decrease the amount of injected TGFβ1 available to cells in the bone marrow.

Some effects on early progenitor cells are observed at 3 hours and these effects are at least partially retained until 48 hrs. This result contrasts somewhat to the effects of TGFβ1 on proliferation of the overall bone marrow cell population suggesting that the progenitors are more sensitive to the effects of TGFβ1 than are other cells in the marrow. This effect is masked in studies of overall proliferation because the progenitor cells represent a relatively small percentage of the total bone marrow cells. The mechanism for the observed antiproliferative effects of TGFβ1 is thought to be at least partially direct since the proliferation of cloned SCA-1 positive stem cells is inhibited in vitro by TGFβ1(Keller et al., unpublished observation).

These data suggest that one clinical use of TGFβ1 would be to protect bone marrow from the effects of myelosuppressive chemotherapeutic drugs or radiation therapy by preventing entry into or removing progenitor cells from cell cycle. Such an approach might allow the use of increased amounts or more frequent administration of myelosuppressive chemotherapeutic drugs or radiotherapy which might increase the therapeutic efficacy achieved with these agents. The success of this type of approach is predicted on the ability of TGFβ1 to block entry into the cell cycle. Published information has shown that TGFβ inhibits the proliferative response of a variety of cells (Spron, M. B. et al., *Nature* 332:217 (1988)) and has been specifically reported to block the transition of B lymphocytes from G1 to S phase of the cell cycle (Soneland, E. B. et al *Exptl Cell Reg.* 171:213 (1987)). These results suggest an ability to inhibit progression through the cell cycle, which would support the concept of using TGFβ as a chemoprotective agent for cycle-active drugs. In this regard, it is also important that the data suggests that the selective inhibitory effects of TGFβ1 on early hematopoietic progenitor cells are temporary and reversible, since long lasting inhibition of early progenitors, which might be achieved by continuous administration of TGFβ1, would be deleterious.

The TGFB compounds of the present invention can be made into pharmaceutical compositions by combination with appropriate medical carriers of diluents. For example, the compounds can be mixed with starch, sugars and other inert ingredients commonly used to make tablets and used as tablets for oral application. The compounds can also be dissolved in oils, propyleneglycol or other solvents commonly used to prepare injectable solutions. For topical application, they can be formulated as ointments or creams.

More specifically, the compounds of the present invention may be formulated into preparations in solid, semisolid, liquid or gaseous form such as tablets, capsules, powders, granules, ointments, solutions, suppositories, and injections, in usual ways for oral or parenteral administration.

The following methods and excipients are merely exemplary and in no way limit the invention.

The TGFβ compounds of the present invention in pharmaceutical dosage form may be used in the form of their pharmaceutically acceptable salts, and also may be used alone or in appropriate association, as well as in combination with other pharmaceutically active compounds.

The TGFβ compounds in the case of oral preparation may be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The TGFβ compounds of the present invention may be formulated into preparations for injections by dissolving, suspending or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds of the invention may be combined with other compounds such as tumor necrosis factor, interferon, interleukin-1, interleukin-6, IL-3, GM-CSF, G-CSF, colony stimulating factor-1.

The desirable dose of the TGFβ compounds of the present invention varies with the subject, drug form, method and period of administration. However, in order to obtain desirable effects, generally it is recommended to administer 0.1 μg to 50 μg, preferably 5 μg to 25 μg/kg, body weight of the TGFβ compounds of the present invention. In terms of composition, compounds should be present between 95 to 100% by weight.

The disclosure of U.S. Ser. No. 06/581,021, filed Feb. 16, 1984 now U.S. Pat. No. 5,04,977 is herein incorporated by reference along with the publications by Keller, J. R. et al., *J. Exp. Med.* 168:737 (1988), Ruscetti, F. et al., "In Monokines and Other Cytokines", Alan Liss Inc., p. 307 (1988), and Sing, G. et al., *Blood* 72:1504 (1988).

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for protecting hematopoietic stem cells, said stem cells retaining at least the multipotential that is characteristic of CFU-GEMM cells, from myelotoxicity of chemotherapeutic drugs which comprises, administering to a subject a therapeutically effective amount of transforming growth factor beta 1 for protecting bone marrow from said myelotoxicity of chemotherapeutic drugs.

2. The method of claim 1, wherein said transforming growth factor beta 1 is administered prior to the administration of said chemotherapeutic drugs.

3. The method of claim 2, wherein the transforming growth factor is administered about 24 hours prior to the administration of said chemotherapeutic drugs.

4. The method of claim 1, wherein said transforming growth factor beta 1 is administered to the subject in an amount of about 2 to 600 μg per kg body weight.

5. The method of claim 1, wherein the mode of administration is by injection.

6. The method of claim 5, wherein injection is via the femoral artery.

7. A method for protecting hematopoietic stem cells, said stem cells retaining at least the multipotential that is characteristic of CFU-GEMM cells, from myelotoxicity of chemotherapeutic drugs which comprises injecting a subject about 24 hours prior to administering chemotherapeutic drugs with 2 to 400 μg per kg of body weight of transforming growth factor beta 1.

8. The method of claim 7, wherein the subject is a mammal.

9. The method of claim 8, wherein the mammal is human.

10. A method for protecting hematopoietic stem cells, said stem cells retaining at least the multipotential that is characteristic of CFU-GEMM cells, from myelotoxicity of chemotherapeutic drugs which comprises, administering to a mammal a therapeutically effective amount of transforming growth factor beta 1 for protecting bone marrow from said myelotoxicity of chemotherapeutic drugs.

11. The method of claim 10, wherein the mammal is human.

12. The method of claim 10, wherein said transforming growth factor beta 1 is administered prior to the administration of said chemotherapeutic drugs.

13. The method of claim 12, wherein the transforming growth factor is administered about 24 hours prior to the administration of said chemotherapeutic drugs.

14. The method of claim 10, wherein said transforming growth factor beta 1 is administered to the mammal in an amount of about 2 to 600 μg per kg body weight.

15. The method of claim 10, wherein the mode of administration is by injection.

16. The method of claim 15, wherein injection is via the femoral artery.

* * * * *